United States Patent
Chen et al.

(10) Patent No.: US 11,740,381 B2
(45) Date of Patent: Aug. 29, 2023

(54) DETERMINATION OF ESTIMATED MAXIMUM RECOVERABLE (EMR) HYDROCARBONS IN UNCONVENTIONAL RESERVOIRS

(71) Applicant: ARAMCO SERVICES COMPANY, Houston, TX (US)

(72) Inventors: Jin-Hong Chen, Katy, TX (US); Stacey M. Althaus, Houston, TX (US); HouZhu Zhang, Houston, TX (US); Hui-Hai Liu, Katy, TX (US); Mohammed Boudjatit, El Kennar (DZ)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/372,161

(22) Filed: Jul. 9, 2021

(65) Prior Publication Data
US 2023/0012861 A1    Jan. 19, 2023

(51) Int. Cl.
*G01V 3/32*      (2006.01)
*G01N 24/08*     (2006.01)
(Continued)

(52) U.S. Cl.
CPC .............. *G01V 3/32* (2013.01); *E21B 49/02* (2013.01); *E21B 49/0875* (2020.05);
(Continued)

(58) Field of Classification Search
CPC ....... G01V 3/32; E21B 49/0875; E21B 49/02; E21B 2200/20; G01N 24/081; G01N 33/241
See application file for complete search history.

(56) References Cited

U.S. PATENT DOCUMENTS

| 6,032,101 A | 2/2000 | Freedman et al. |
| 10,488,352 B2 | 11/2019 | Chen et al. |

(Continued)

FOREIGN PATENT DOCUMENTS

| CN | 119369773 | * | 1/2022 | ............ G01B 11/30 |
| WO | 2011/133859 A1 | | 10/2011 | |
| WO | 2013/158382 A1 | | 10/2013 | |

OTHER PUBLICATIONS

Somayeh Karimi "Capillary Pressure, Fluid Distribution, and Oil Recovery in Preserved Middle Bakken Cores" SPE-185095-MS Oklahoma City Oil and Gas Sumposium held Oklahome City, Oklahome, USA Mar. 27-31, 2017, p. 1-24 (Year: 2017).*

(Continued)

*Primary Examiner* — Michael J Dalbo
*Assistant Examiner* — Kaleria Knox
(74) *Attorney, Agent, or Firm* — Osha Bergman Watanabe & Burton LLP

(57) ABSTRACT

A method for determining maximum recoverable hydrocarbon (EMR) in a tight reservoir is disclosed. The method includes determining, based on downhole logs, a total measure of hydrocarbon amount within the tight reservoir, determining, by at least attributing fluid loss during core surfacing of the core sample to hydrocarbons, a non-recoverable measure of hydrocarbon amount within a core sample of the tight reservoir, and determining an EMR measure based on the total measure of hydrocarbon amount and the non-recoverable measure of hydrocarbon amount, wherein during the core surfacing pore pressure reduces from a reservoir condition to a surface condition.

20 Claims, 5 Drawing Sheets

(51) Int. Cl.
  *E21B 49/02* (2006.01)
  *E21B 49/08* (2006.01)
  *G01N 33/24* (2006.01)
(52) U.S. Cl.
  CPC ......... *G01N 24/081* (2013.01); *G01N 33/241* (2013.01); *E21B 2200/20* (2020.05)

(56) References Cited

U.S. PATENT DOCUMENTS

| | | | |
|---|---|---|---|
| 2004/0016289 A1* | 1/2004 | Zamfes | G01N 15/042 |
| | | | 73/38 |
| 2013/0200890 A1* | 8/2013 | Hursan | G01V 3/32 |
| | | | 324/303 |
| 2018/0081077 A1 | 3/2018 | Chen et al. | |
| 2018/0258763 A1* | 9/2018 | King, Jr. | G01N 24/081 |
| 2019/0027087 A1* | 1/2019 | Holland | G09G 3/2096 |
| 2020/0363354 A1* | 11/2020 | King | G01N 24/081 |
| 2020/0363357 A1* | 11/2020 | Kortunov | G01N 24/081 |

OTHER PUBLICATIONS

Howard C. Pyle "Core Analysis", pp. 33-61; Manuscript received at the office of the Institute Oct. 14, 1938. Issued as T.P. 1024 in Petroleum Technology, Feb. 1939. * Union Oil Company of California, Los Angeles, California (Year: 1938).*
Karimi, Somayeh et al., "Capillary Pressure, Fluid Distribution, and Oil Recovery in Preserved Middle Bakken Cores"; Proceedings of the SPE Oklahoma City Oil and Gas Symposium; Paper No. SPE-185095-MS; pp. 1-26; Mar. 27-31, 2017 (26 pages).

* cited by examiner a). Reservoir Condition b). Surface Condition

DETERMINATION OF ESTIMATED MAXIMUM RECOVERABLE (EMR) HYDROCARBONS IN UNCONVENTIONAL RESERVOIRS

BACKGROUND

An unconventional reservoir consists of an ultra-tight source rock, trap and seal containing organic rich matter that has reached thermal maturity without migration. Typical unconventional reservoirs are tight-gas sands, coal-bed methane, heavy oil, and gas shales. The unconventional reservoir typically has such low permeability that massive hydraulic fracturing is necessary to produce hydrocarbons. The unconventional reservoir is also referred to as a tight reservoir throughout this disclosure.

Hydrocarbon reserve evaluation is a major concern for oil and gas operating companies to make critical investment decisions. Estimated ultimate recovery (EUR) is the term referring to the quantities of hydrocarbons which are estimated to be potentially recoverable from an accumulation, plus those quantities already produced therefrom. IHCIP is the term referring to initial hydrocarbon-in-place. Recovery factor (RF) may be used to characterize the production rate for a reservoir according to $$RF = \frac{EUR}{IHCIP} \quad (1)$$

Determining RF for unconventional shale or tight reservoirs is extremely challenging because these reservoirs have very low permeability, and thus require hydraulic fracturing to stimulate production. In this case, it is very difficult to determine the stimulated reservoir volume (SRV) which is needed to calculate the IHCIP and EUR. In addition, EUR, in many cases, is obtained by fitting short term production data, which can introduce large errors. As a result, estimating recovery factor for unconventional reservoirs is very challenging and the results may not be reliable.

SUMMARY

In general, in one aspect, the invention relates to a method for determining maximum recoverable hydrocarbon (EMR) in a tight reservoir. The method includes determining, based on downhole logs, a total measure of hydrocarbon amount within the tight reservoir, determining, by at least attributing fluid loss during core surfacing of the core sample to hydrocarbons, a non-recoverable measure of hydrocarbon amount within a core sample of the tight reservoir, and determining an EMR measure based on the total measure of hydrocarbon amount and the non-recoverable measure of hydrocarbon amount, wherein during the core surfacing pore pressure reduces from a reservoir condition to a surface condition.

In general, in one aspect, the invention relates to a system that includes a tight reservoir, a data repository for storing downhole logs of the tight reservoir, and an analysis and modeling engine comprising functionality for determining, based on the downhole logs, a total measure of hydrocarbon amount within the tight reservoir, determining, by at least attributing fluid loss during core surfacing of the core sample to hydrocarbons, a non-recoverable measure of hydrocarbon amount within a core sample of the tight reservoir, and determining an EMR measure based on the total measure of hydrocarbon amount and the non-recoverable measure of hydrocarbon amount, wherein during the core surfacing pore pressure reduces from a reservoir condition to a surface condition.

In general, in one aspect, the invention relates to a non-transitory computer readable medium (CRM) storing computer readable program code for determining maximum recoverable hydrocarbon (EMR) in a tight reservoir. The computer readable program code, when executed by a computer, includes functionality for determining, based on downhole logs, a total measure of hydrocarbon amount within the tight reservoir, determining, by at least attributing fluid loss during core surfacing of the core sample to hydrocarbons, a non-recoverable measure of hydrocarbon amount within a core sample of the tight reservoir, and determining an EMR measure based on the total measure of hydrocarbon amount and the non-recoverable measure of hydrocarbon amount, wherein during the core surfacing pore pressure reduces from a reservoir condition to a surface condition.

Other aspects and advantages will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Embodiments of the invention provide a method, a system, and a non-transitory computer readable medium for determining maximum recoverable hydrocarbon (EMR) in a tight reservoir. In one or more embodiments of the invention, a total measure of hydrocarbon amount within the tight reservoir is determined based on downhole logs, and a non-recoverable measure of hydrocarbon amount within a core sample of the tight reservoir is determined by attributing fluid loss during core surfacing of the core sample to hydrocarbons. During the core surfacing, pore pressure reduces from a reservoir condition to a surface condition. Accordingly, an EMR measure is determined based on the total measure of hydrocarbon amount and the non-recoverable measure of hydrocarbon amount.

Figure 1A:
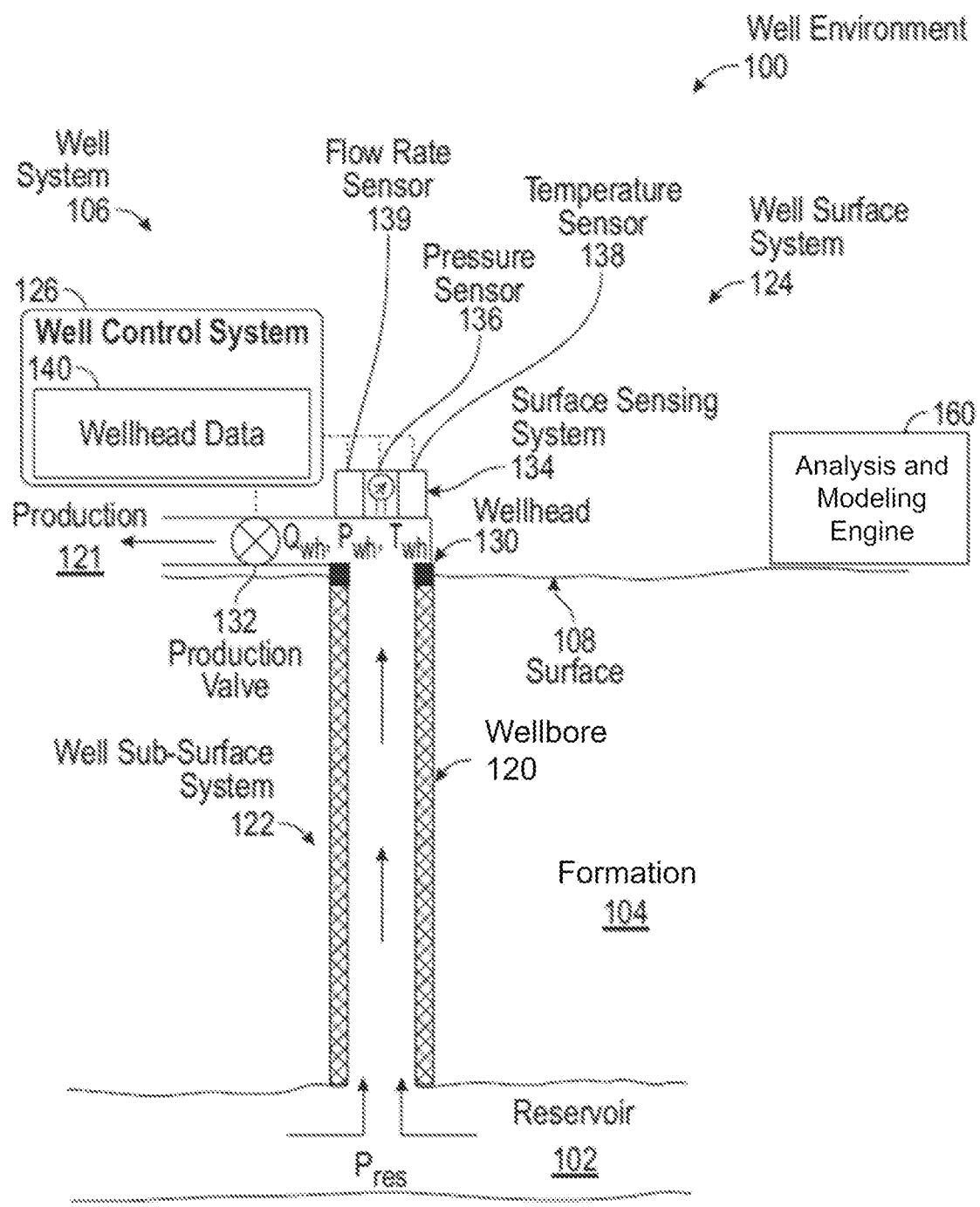
FIGS. 1A-1B show systems in accordance with one or more embodiments.

FIG. 1A shows a schematic diagram in accordance with one or more embodiments. More specifically, FIG. 1A illustrates a well environment (100) that includes a hydrocarbon reservoir ("reservoir") (102) located in a subsurface formation ("formation") (104) and a well system (106). The formation (104) may include a porous formation that resides underground, beneath the Earth's surface ("surface") (108). In the case of the well system (106) being a hydrocarbon well, the reservoir (102) may include a portion of the formation (104). The formation (104) and the reservoir (102) may include different layers (referred to as subterranean intervals or geological intervals) of rock having varying characteristics, such as varying degrees of permeability, porosity, capillary pressure, and resistivity. In other words, a subterranean interval is a layer of rock having consistent permeability, porosity, capillary pressure, resistivity, and/or other characteristics. For example, the reservoir (102) may be an unconventional reservoir or tight reservoir. In the case of the well system (106) being operated as a production well, the well system (106) may facilitate the extraction of hydrocarbons (or "production") from the reservoir (102).

In some embodiments, the well system (106) includes a wellbore (120), a well sub-surface system (122), a well surface system (124), and a well control system ("control system") (126). The control system (126) may control various operations of the well system (106), such as well production operations, well completion operations, well maintenance operations, and reservoir monitoring, assessment and development operations. In some embodiments, the control system (126) includes a computer system that is the same as or similar to that of computer system (400) described below in FIGS. 4A and 4B and the accompanying description.

The wellbore (120) may include a bored hole that extends from the surface (108) into a target zone (i.e., a subterranean interval) of the formation (104), such as the reservoir (102). An upper end of the wellbore (120), terminating at or near the surface (108), may be referred to as the "up-hole" end of the wellbore (120), and a lower end of the wellbore, terminating in the formation (104), may be referred to as the "down-hole" end of the wellbore (120). The wellbore (120) may facilitate the circulation of drilling fluids during drilling operations, the flow of hydrocarbon production ("production") (121) (e.g., oil and gas) from the reservoir (102) to the surface (108) during production operations, the injection of substances (e.g., water) into the formation (104) or the reservoir (102) during injection operations, or the communication of monitoring devices (e.g., logging tools) into the formation (104) or the reservoir (102) during monitoring operations (e.g., during in situ logging operations). For example, the logging tools may include logging-while-drilling tool or logging-while-tripping tool for obtaining downhole logs.

In some embodiments, during operation of the well system (106), the control system (126) collects and records wellhead data (140) for the well system (106). The wellhead data (140) may include, for example, a record of measurements of wellhead pressure ($P_{wh}$) (e.g., including flowing wellhead pressure), wellhead temperature ($T_{wh}$) (e.g., including flowing wellhead temperature), wellhead production rate ($Q_{wh}$) over some or all of the life of the well (106), and water cut data. In some embodiments, the measurements are recorded in real-time, and are available for review or use within seconds, minutes, or hours of the condition being sensed (e.g., the measurements are available within 1 hour of the condition being sensed). In such an embodiment, the wellhead data (140) may be referred to as "real-time" wellhead data (140). Real-time wellhead data (140) may enable an operator of the well (106) to assess a relatively current state of the well system (106), and make real-time decisions regarding development of the well system (106) and the reservoir (102), such as on-demand adjustments in regulation of production flow from the well.

In some embodiments, the well sub-surface system (122) includes casing installed in the wellbore (120). For example, the wellbore (120) may have a cased portion and an uncased (or "open-hole") portion. The cased portion may include a portion of the wellbore having casing (e.g., casing pipe and casing cement) disposed therein. The uncased portion may include a portion of the wellbore not having casing disposed therein. In embodiments having a casing, the casing defines a central passage that provides a conduit for the transport of tools and substances through the wellbore (120). For example, the central passage may provide a conduit for lowering logging tools into the wellbore (120), a conduit for the flow of production (121) (e.g., oil and gas) from the reservoir (102) to the surface (108), or a conduit for the flow of injection substances (e.g., water) from the surface (108) into the formation (104). In some embodiments, the well sub-surface system (122) includes production tubing installed in the wellbore (120). The production tubing may provide a conduit for the transport of tools and substances through the wellbore (120). The production tubing may, for example, be disposed inside casing. In such an embodiment, the production tubing may provide a conduit for some or all of the production (121) (e.g., oil and gas) passing through the wellbore (120) and the casing.

In some embodiments, the well surface system (124) includes a wellhead (130). The wellhead (130) may include a rigid structure installed at the "up-hole" end of the wellbore (120), at or near where the wellbore (120) terminates at the Earth's surface (108). The wellhead (130) may include structures (called "wellhead casing hanger" for casing and "tubing hanger" for production tubing) for supporting (or "hanging") casing and production tubing extending into the wellbore (120). Production (121) may flow through the wellhead (130), after exiting the wellbore (120) and the well sub-surface system (122), including, for example, the casing and the production tubing. In some embodiments, the well surface system (124) includes flow regulating devices that are operable to control the flow of substances into and out of the wellbore (120). For example, the well surface system (124) may include one or more production valves (132) that are operable to control the flow of production (121). For example, a production valve (132) may be fully opened to enable unrestricted flow of production (121) from the wellbore (120), the production valve (132) may be partially opened to partially restrict (or "throttle") the flow of production (121) from the wellbore (120), and production valve (132) may be fully closed to fully restrict (or "block") the flow of production (121) from the wellbore (120), and through the well surface system (124).

In some embodiments, the wellhead (130) includes a choke assembly. For example, the choke assembly may include hardware with functionality for opening and closing the fluid flow through pipes in the well system (106). Likewise, the choke assembly may include a pipe manifold that may lower the pressure of fluid traversing the wellhead.

As such, the choke assembly may include set of high pressure valves and at least two chokes. These chokes may be fixed or adjustable or a mix of both. Redundancy may be provided so that if one choke has to be taken out of service, the flow can be directed through another choke. In some embodiments, pressure valves and chokes are communicatively coupled to the well control system (126). Accordingly, a well control system (126) may obtain wellhead data regarding the choke assembly as well as transmit one or more commands to components within the choke assembly in order to adjust one or more choke assembly parameters.

Keeping with FIG. 1A, in some embodiments, the well surface system (124) includes a surface sensing system (134). The surface sensing system (134) may include sensors for sensing characteristics of substances, including production (121), passing through or otherwise located in the well surface system (124). The characteristics may include, for example, pressure, temperature and flowrate of production (121) flowing through the wellhead (130), or other conduits of the well surface system (124), after exiting the wellbore (120).

In some embodiments, the surface sensing system (134) includes a surface pressure sensor (136) operable to sense the pressure of production (121) flowing through the well surface system (124), after it exits the wellbore (120). The surface pressure sensor (136) may include, for example, a wellhead pressure sensor that senses a pressure of production (121) flowing through or otherwise located in the wellhead (130). In some embodiments, the surface sensing system (134) includes a surface temperature sensor (138) operable to sense the temperature of production (121) flowing through the well surface system (124), after it exits the wellbore (120). The surface temperature sensor (138) may include, for example, a wellhead temperature sensor that senses a temperature of production (121) flowing through or otherwise located in the wellhead (130), referred to as "wellhead temperature" ($T_{wh}$). In some embodiments, the surface sensing system (134) includes a flowrate sensor (139) operable to sense the flowrate of production (121) flowing through the well surface system (124), after it exits the wellbore (120). The flowrate sensor (139) may include hardware that senses a flowrate of production (121) ($Q_{wh}$) passing through the wellhead (130).

Prior to completing the well system (106) or for identifying candidate locations to drill a new well, hydrocarbon reserves may be estimated to evaluate the economic potential of completing the formation drilling to access an oil or gas reservoir, such as the reservoir (102). Estimating the hydrocarbon reserve, such as the EUR, of a tight reservoir is particularly important due to the expense of hydraulic fracturing operations necessary to produce hydrocarbons. The well system (106) further includes an analysis and modeling engine (160). For example, the analysis and modeling engine (160) may include hardware and/or software with functionality to analyze the well log data, the core sample data, and/or other types of data to generate and/or update one or more reservoir models and corresponding hydrocarbon reserve estimates of the reservoir (102).

In one or more embodiments of the invention, the analysis and modeling engine (160) includes the functionality to generate hydrocarbon reserve estimates for unconventional source rock or tight reservoirs based on an estimated maximum recoverable (EMR) measure. The terms "EMR" and "EMR measure" are used interchangeably throughout this disclosure. EMR is defined as $$EMR = \frac{MRHC}{ISHC} \quad (2)$$

where MRHC is the maximum recoverable hydrocarbon when the bottomhole pressure is reduced to 1 standard atmosphere (ATM), and ISHC is the in-situ hydrocarbon in the source rocks. In contrast to determining EUR and IHCIP in the RF method, determining MRHC and ISHC is through measured parameters from log and core without the difficulty to accurately determine the stimulated reservoir volume (SRV) for EUR and IHCIP.

The method of generating hydrocarbon reserve estimates based on the EMR is referred to as the EMR method. The EMR method is based on measurable data from downhole logs and/or extracted cores, and accounts for reservoir heterogeneity, which can be quite high for the tight reservoir, such as a source rock reservoir. The EMR method advantageously provides improvements in the processing time and estimate accuracy over the current industry practice of using recovery factor (RF) based method.

While the analysis and modeling engine (160) is shown at a well site in FIG. 1A, those skilled in the art will appreciate that the analysis and modeling engine (160) may also be remotely located away from well site.

Figure 1B:
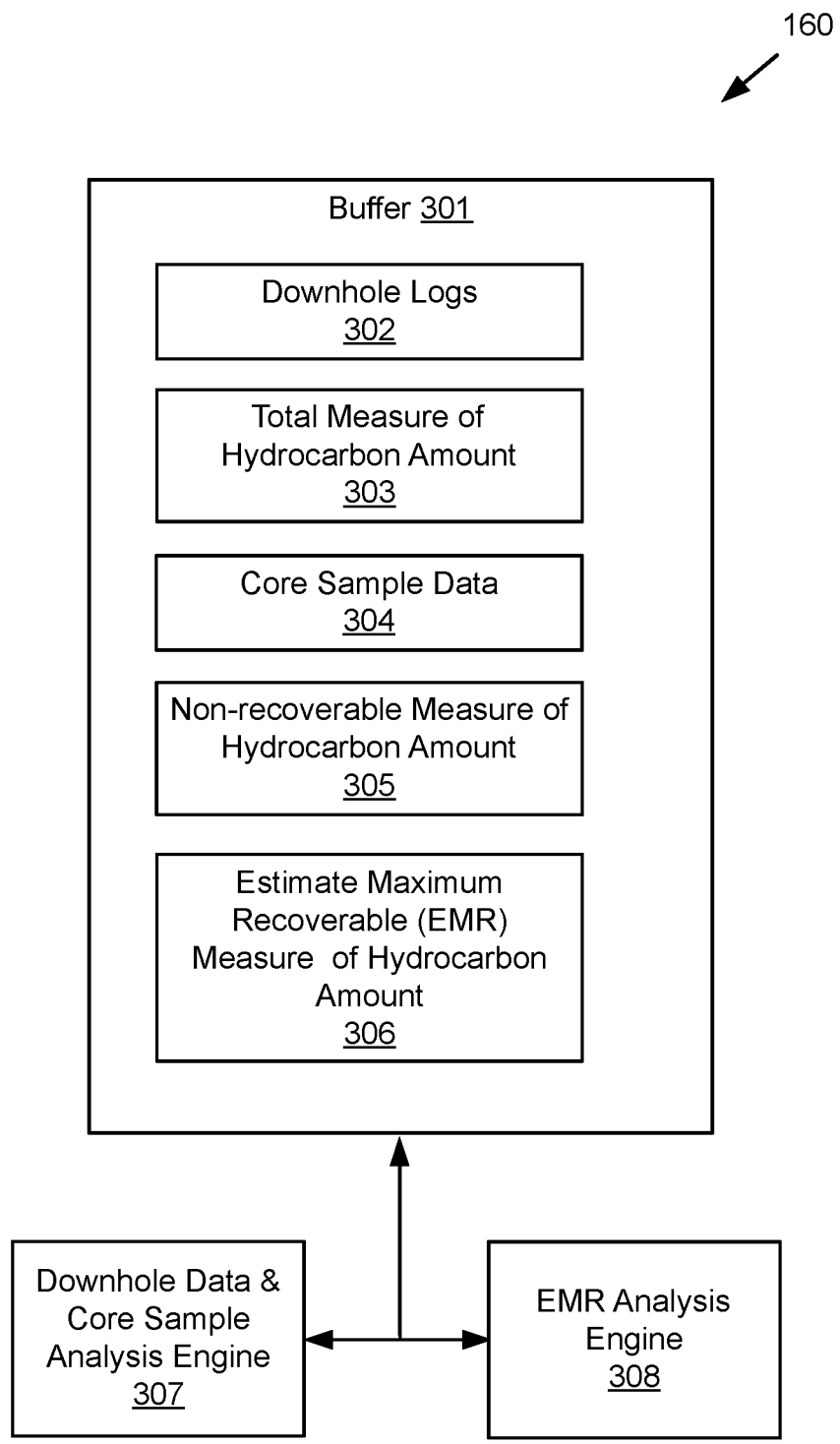

Turning to FIG. 1B, FIG. 1B shows a schematic diagram in accordance with one or more embodiments. Specifically, FIG. 1B illustrates details of the analysis and modeling engine (160) depicted in FIG. 1A above. In one or more embodiments, one or more of the modules and/or elements shown in FIG. 1B may be omitted, repeated, and/or substituted. Accordingly, embodiments of the invention should not be considered limited to the specific arrangements of modules and/or elements shown in FIG. 1B. In one or more embodiments of the invention, although not shown in FIG. 1B, the analysis and modeling engine (160) may include a computer system that is similar to the computer system (400) described below with regard to FIGS. 4A and 4B and the accompanying description.

As shown in FIG. 1B, the analysis and modeling engine (160) has multiple components, including, for example, a buffer (301), a downhole data and core sample analysis engine (307), and an EMR analysis engine (307). Each of these components (301, 307, 308) may be implemented in hardware (i.e., circuitry), software, or any combination thereof. Further, each of these components (301, 307, 308) may be located on the same computing device (e.g., personal computer (PC), laptop, tablet PC, smart phone, multifunction printer, kiosk, server, etc.) or on different computing devices connected by a network of any size having wired and/or wireless segments. In one or more embodiments, these components may be implemented using the computing system (400) described below in reference to FIGS. 4A and 4B. Each of these components is discussed below.

In one or more embodiments of the invention, the buffer (301) is configured to store data such as downhole logs (302), a total measure of hydrocarbon amount (303), core sample data (304), a non-recoverable measure of hydrocarbon amount (305), and an estimated maximum recoverable (EMR) measure of hydrocarbon amount (306). Downhole logs (302) are measurements of physical, chemical, and structural properties of the formation (104) surrounding the wellbore (120) that are made during or after completion of drilling. The data are rapidly collected, continuous with depth (at vertical sampling intervals ranging from 2.5 to 150 mm), and measured in-situ using the logging tools, such as a logging-while-drilling tool or a logging-while-tripping tool.

The total measure of hydrocarbon amount (303) is the quantity of hydrocarbons measured in the reservoir (102). The core sample data (304) includes measured characteristics of the core sample, such as porosity, permeability, hydrogen index, etc. The non-recoverable measure of hydrocarbon amount (305) is a measure (e.g., a percentage) of hydrocarbons retained in the tight reservoir that cannot be extracted without excessively difficult processes. The EMR (306) is a measure (e.g., a percentage) of hydrocarbons that can be extracted from the tight reservoir without excessively difficult processes.

In one or more embodiments of the invention, the downhole data and core sample analysis engine (307) is configured to generate the total measure of hydrocarbon amount (303) based on the downhole logs (302), and generate the non-recoverable measure of hydrocarbon amount (305) based on the core sample data (304). The EMR analysis engine (308) is configured to generate the EMR (306) based on the total measure of hydrocarbon amount (303) and the non-recoverable measure of hydrocarbon amount (305). In one or more embodiments, the downhole data and core sample analysis engine (307) and the EMR analysis engine (308) perform the functions described above using the method workflow described in reference to FIG. 2 below. An example of performing the method workflow using the downhole data and core sample analysis engine (307) and the EMR analysis engine (308) is described in reference to FIG. 3 below.

Although the analysis and modeling engine (160) is shown as having three components (301, 306, 307), in one or more embodiments of the invention, the analysis and modeling engine (160) may have more or fewer components. Furthermore, the functions of each component described above may be split across components or combined in a single component. Further still, each component (301, 306, 307) may be utilized multiple times to carry out an iterative operation.

Figure 2:
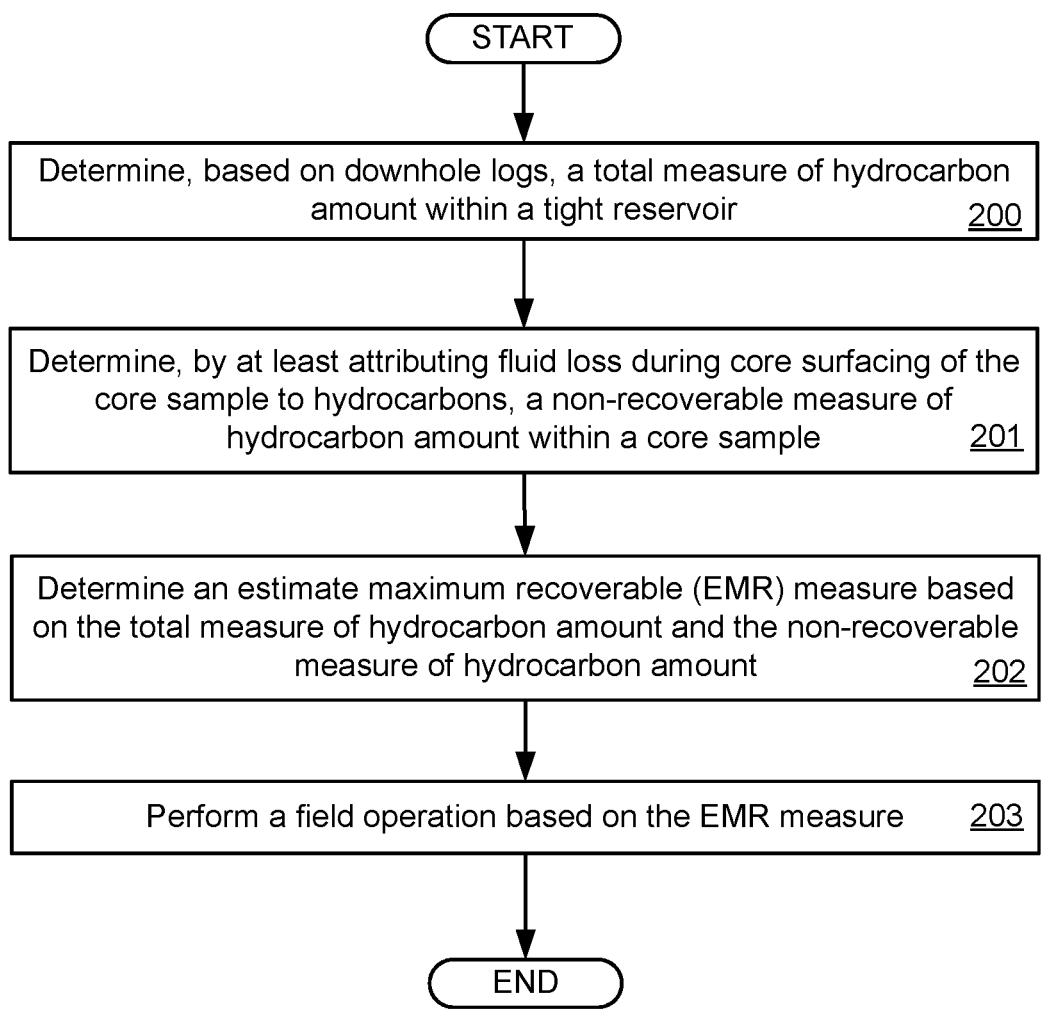
FIG. 2 shows a flowchart in accordance with one or more embodiments.

FIG. 2 shows a flowchart in accordance with one or more embodiments. One or more blocks in FIG. 2 may be performed using one or more components as described in FIGS. 1A-1B. While the various blocks in FIG. 2 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

Initially in Block 200, a total measure of hydrocarbon amount (i.e., ISHC) within a tight reservoir is determined based on downhole logs. For example, as depicted in FIG. 1B above, the total measure of hydrocarbon amount (303) may be determined based on the downhole logs (302). Many techniques have been developed to determine the total measure of hydrocarbon amount based on downhole logs, such as nuclear magnetic resonance (NMR) logs. In one or more embodiments, laboratory NMR analysis is used to determine water relaxation curve for a core sample of the tight reservoir. The water relaxation curve for the core sample is then compared with the relaxation curve derived from NMR logging data of the tight reservoir to determine a difference in water relaxation. Total hydrocarbon amount within the tight reservoir is then determined based on the difference in water relaxation. [

Specific details of computing the total measure of hydrocarbon amount within the tight reservoir are described in reference to FIG. 3 below. For example, the total measure of hydrocarbon amount may be determined based on Eq. (5) described in reference to FIG. 3 below. In particular, the total measure of hydrocarbon amount within the tight reservoir is computed as $\phi_{HC}$ of Eq. (5).

In Block 201, a non-recoverable measure of hydrocarbon amount within a core sample of the tight reservoir is determined by at least attributing fluid loss during core surfacing of the core sample to hydrocarbons. Cores from a tight reservoir (e.g., unconventional source rock reservoir) with extremely low permeability (e.g., in the nano-Darcy range) have minimal or no contamination from drilling mud, in contrast to cores for conventional reservoir with much larger permeability and prone to significant mud invasion. Therefore, the fluids inside the source rock cores from tight reservoirs are considered native. However, during the surfacing of cores from the subsurface reservoir, the pore fluid pressure reduces along with the reduction of the external pressure, from the reservoir pressure of thousands of pound per square inch (psi) to the surface pressure of approximately 14.5 psi. As a result, part of the pore fluids is lost during core surfacing because of pore pressure reduction.

The change of net water in the core sample during surfacing is approximated as negligible for unconventional tight reservoirs for the following reasons. First, in-situ water in the source rocks is likely irreducible because the majority of pore sizes in unconventional tight reservoirs are smaller than 1 micro-meter (µm) and the pore throats controlling the brine flow are even smaller. Second, the total possible volume change of the pore water due to pressure and temperature change is generally no more than 10% and thus will not result in a large error to the final result. Therefore, the fluid loss or change during the core surfacing is attributed to hydrocarbons when the pore pressure reduces from reservoir condition to the surface condition. The reservoir condition refers to pressure (e.g., 3000 psi), temperature (e.g., 180° F.), and/or other characteristics in the reservoir. The surface condition refers to pressure (e.g., 14.5 psi), temperature (e.g., 70° F.), and/or other characteristics at the surface.

After core surfacing, the hydrocarbons that remain in the cores at 14.5 psi and ground temperature represent the irreducible or non-producible hydrocarbons. These hydrocarbons cannot be produced by pressure reduction without application of enhanced recovery. In this context, the amount of hydrocarbons that remain in the cores after core surfacing is referred to as the non-recoverable measure of hydrocarbon amount, which is measured using laboratory techniques, such as NMR or dean stark extraction. Correspondingly, the net loss of hydrocarbon during the surfacing of cores represents the maximum recoverable hydrocarbons from a tight reservoir.

Specific details of computing the non-recoverable measure of hydrocarbon amount in the core sample are described in reference to FIG. 3 below. For example, the non-recoverable measure of hydrocarbon amount may be determined based on Eq. (6) described in reference to FIG. 3 below. In particular, the non-recoverable measure of hydrocarbon amount in the core sample is computed as $\phi_{HC}^{rem}$ of Eq. (6).

In Block 202, the EMR measure is determined based on the total measure of hydrocarbon amount determined in Block 200 and the non-recoverable measure of hydrocarbon amount determined in Block 201. Based on the foregoing, the estimated maximum recoverable (EMR) hydrocarbons may be determined by pressure reduction, i.e., EMR is the difference of total hydrocarbon within the reservoir and the non-movable hydrocarbons in the preserved cores. The former is measured through downhole logs and the latter is measured using laboratory technologies. Specific details of computing the EMR are described in reference to FIG. 3 below. For example, the EMR may be determined based on one or more of Eq. (10), Eq (11), and Eq. (12) described in reference to FIG. 3 below.

In Block 203, a field operation is performed based on the EMR measure. For example, the well may be completed if the EMR measure exceeds a pre-determined threshold that indicates the tight reservoir as financially viable for hydrocarbon production. Other examples of the field operation may include drilling operation, production operation, and/or other operations for accessing the tight reservoir to produce hydrocarbons.

Figure 3:
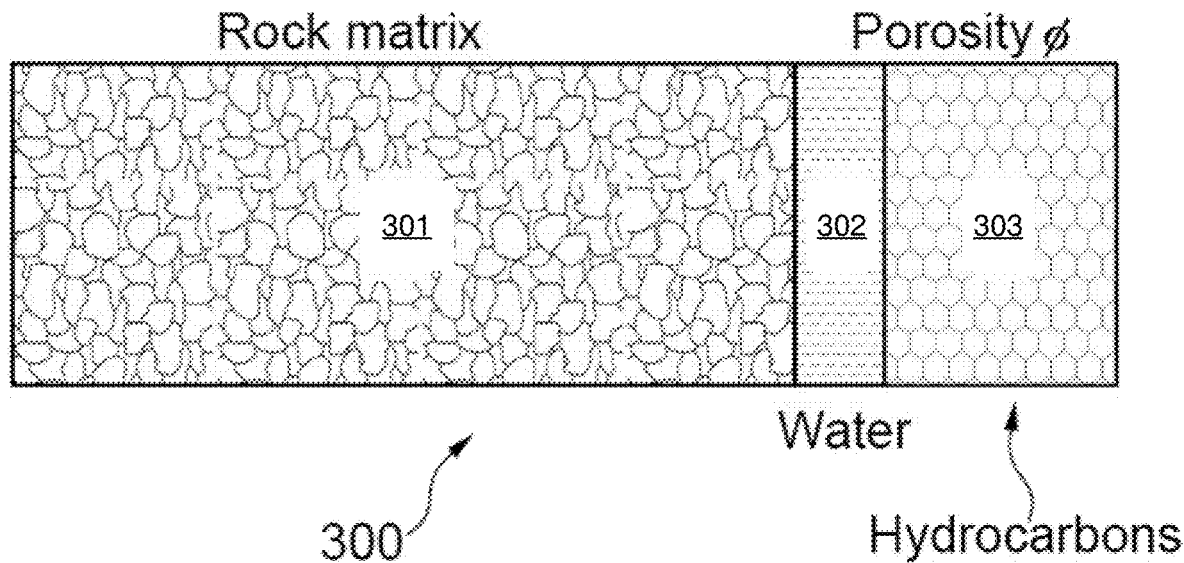
FIG. 3 shows an example in accordance with one or more embodiments.
Figure 3:
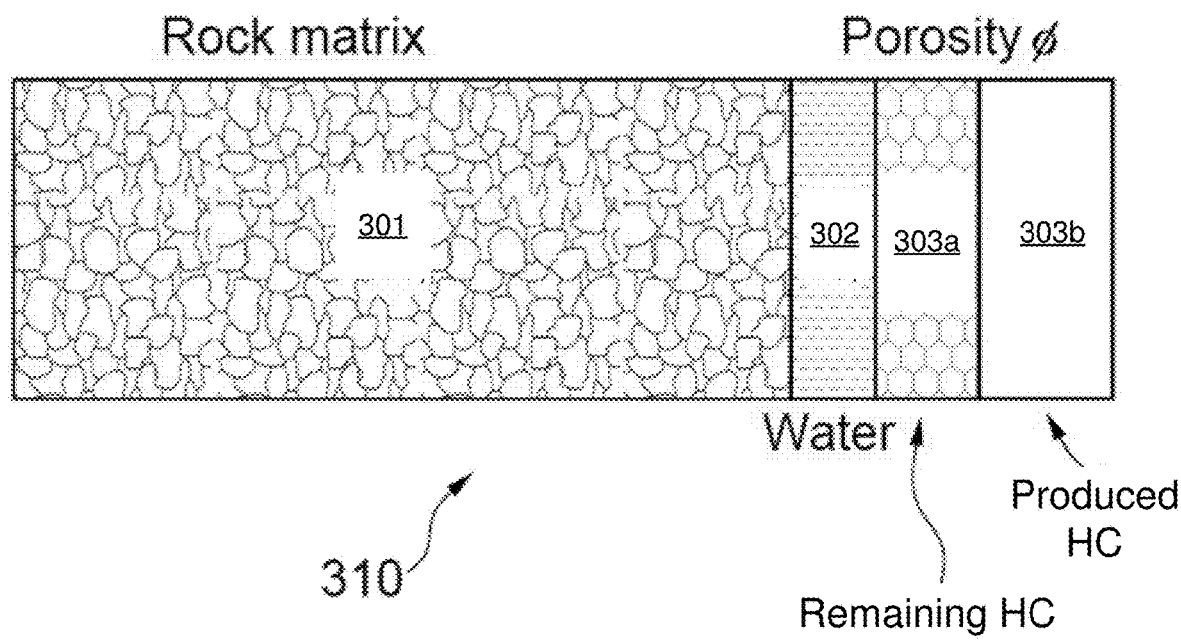

FIG. 3 shows an example in accordance with one or more embodiments. The example shown in FIG. 3 is based on the system and method described in reference to FIGS. 1A-1B and 2 above. As noted above, during the core surfacing, pore pressure reduces from a reservoir condition to a surface condition. The example shown in Fig. 3 illustrates the volumetric partition (301) of source rock at the reservoir condition and the volumetric partition (302) of source rock at the surface condition. At the reservoir condition, the volumetric partition (300) includes three portions (301, 302, 303) that represent respective volume percentages of rock matrix, water, and hydrocarbon in the source rock where the partitions (302, 303) correspond to the pore volume percentage (i.e., porosity) of the source rock. The partitions (302, 303) are denoted as $\phi_w$ and $\phi_{HC}$, respectively, in the mathematical formula below. The volumetric partition (310) at the surface condition is similar to the volumetric partition (300) with the exception that the hydrocarbon partition (303) is divided into partitions (303a, 303b). The partition (303a) represents the percentage of pore volume retaining hydrocarbons after the core sample is brought to the surface. The partition (303b) represents the percentage of pore volume where hydrocarbons have escaped after the core sample is brought to the surface. The partitions (303a, 303b) are denoted as $\phi_{HC}^{rem}$ and $\phi_{HC}^{prod}$, respectively, in the mathematical formulas below.

At the reservoir condition, the total porosity $\phi$ is $$\phi = \phi_w + \phi_{HC} \tag{1}$$

where $\phi_w$ and $\phi_{HC}$ are the volume of water and hydrocarbon in porosity unit, respectively. In particular, 100 porosity units (pu)=100%. At the surface, the net water volume percentage (302) is considered the same as in the reservoir. The net loss of fluid is attributed to hydrocarbons and thus the porosity partition is expressed as $$\phi = \phi_w + \phi_{HC}^{rem} + \phi_{HC}^{prod} \tag{2}$$

where $\phi_{HC}^{rem}$ and $\phi_{HC}^{prod}$ are remaining and produced hydrocarbon amounts expressed in porosity unit, respectively, at surface condition. If the possible porosity change is neglected at downhole and surface conditions of the rock, the produced hydrocarbon is estimated by subtracting Eq. (2) from Eq. (1).

Note that this method cannot be used for conventional reservoirs because mud invasion is unavoidable during core surfacing for conventional rocks with large permeability. As a result, the acquired cores include drilling mud and surface condition scenario b) shown in FIG. 3 is not true anymore.

An example workflow to measure the EMR using measured data at downhole and/or at surface from different measurement methods is described in Step 1) through step 6) below.

Step 1) The total fluid volume downhole can be measured using different logging methods. Among them, NMR logging is one of the best methods for source rock reservoirs and used as an example here. In the reservoir, NMR log measures the total hydrogen and the measured NMR signal can be expressed as $$\phi_w = v_w / HI_w^{res}, \phi_{HC} = v_{HC} / HI_{HC}^{res} \tag{3}$$

where $v_w$ and $v_{HC}$ are the measured NMR signals from water and hydrocarbon calibrated to volume unit; $HI_w^{res}$ and $HI_{HC}^{res}$ are the hydrogen indices of water and hydrocarbon at reservoir condition, respectively, that are determined based on the NMR logging data; $HI_w^{res} \approx 1$ and $HI_{HC}^{res} \approx 1$ for liquid hydrocarbon; and $HI_{HC}^{res} < 1$ if reservoir fluids include gas in the rock pore system at the reservoir condition.

Step 2) At the surface condition, there are also different methods to measure the irreducible water and hydrocarbon in the preserved whole cores. For example, U.S. patent Ser. No. 10/488,352B2 describes a whole core NMR method, which is a non-destructive way to measure the total fluids in unconventional shale rocks and to measure the remaining fluids in the cores. NMR is insensitive to the gas because of extreme low density of gas and thus only measures the liquid in the cores. The measured partial porosity in preserved cores is then $$\phi_{pres.core}^{NMR} = \phi_w + \phi_{HC}^{res} \tag{4}$$

Note Eq. (4) assumes that hydrogen indices for both water and liquid hydrocarbon are approximately 1 at laboratory condition.

Step 3) The produced hydrocarbon, expressed in porosity unit, is then the total measured fluid volume at the reservoir subtracted by the fluid in the preserved cores $\phi_{pres.core}^{NMR}$ $$\phi_{HC}^{prod} = v_w + v_{HC} - \phi_{pres.core}^{NMR} \tag{5}$$

where $\phi_{pres.core}^{NMR}$ is the fluid volume percentage in the preserved core measured in porosity unit using an NMR method. The estimated produced hydrocarbon using this method, as discussed above, is the ultimate amount that can be produced. As such, the EMR is estimated as $$EMR = \phi_{HC}^{prod} / v_{HC} \tag{6}$$

Or $$EMR = (v_w + v_{HC} - \phi_{pres.core}^{NMR}) / v_{HC} \tag{7}$$

Inserting Eq. (3) into Eq. (7) and using $HI_w^{res} \approx 1$ results in $$EMR = (\phi_w + \phi_{HC} HI_{HC}^{res} - \phi_{pres.core}^{NMR}) / \phi_{HC} HI_{HC}^{res} \tag{8}$$

Eq. (10) provides a generic way to measure the EMR from downhole log data and surface measurement of preserved cores. In Eq. (10), $\phi_w$ and $\phi_{HC}$ denote a water volume percentage and a hydrocarbon volume percentage, respectively, at reservoir condition that could be determined based on nuclear magnetic resonance (NMR) logging data of the downhole logs, $\phi_{pres.core}^{NMR}$ denotes a fluid volume percentage in the core sample measured at surface condition possibly using an NMR method, and $HI_{HC}^{res}$ denotes a hydrogen index of the hydrocarbons.

Step 4) Using water saturation $S_w = \phi_w / \phi$, Eq. (8) becomes $$EMR = [S_w + (1-S_w) HI_{HC}^{res} - \phi_{pres.core}^{NMR} / \phi] / (1-S_w) HI_{HC}^{res} \tag{9}$$

In addition to the total fluid estimated from preserved whole cores, three parameters about the source rock reservoir, $\phi$, $S_w$, and $HI_{HC}^{res}$, are needed to estimate EMR. These parameters can be measured using downhole logs or in combination with laboratory measurement. Water saturation may be deduced from downhole log data. However, if downhole log data is not available, it may be obtained in laboratory measurement of well-preserved samples. In Eq. (11), $S_w$ denotes a water saturation measured at reservoir condition using the downhole logs, $\phi_{pres.core}^{NMR}$ denotes a fluid volume percentage in the core sample measured at surface condition using an NMR method, and $HI_{HC}^{res}$ denotes a hydrogen index of the hydrocarbons.

Step 5) As described above, the method of estimating EMR is based on the use of rock samples and clearly depends on the reservoir heterogeneity or lamination. An EMR is determined for each sample taken at different depth of a well. The overall EMR is determined by taking the simple average of all the data measured at different depths.

Step 6) For a special case, if the reservoir only has liquids, i.e., all the hydrocarbons and water are in liquid states, the method described above can be significantly simplified. In this case, $HI_{HC}^{res} \approx 1$, Eq. (9) is simplified to $$EMR=(1-\phi_{pres.core}^{NMR}/\phi)/(1-S_w) \qquad (10)$$

In Eq. (12), where $S_w$ denotes a water saturation measured at reservoir condition using the downhole logs, $\phi_{pres.core}^{NMR}$ denotes a fluid volume percentage in the core sample measured at surface condition using an NMR method.

This significantly simplifies the requirement to determine EMR because all the parameters in Eq. (10) can now be obtained from measurement of the extracted rocks using different methods. For example, porosity and water saturation may be obtained from the crushed shale (GRI) method or using a combination of NMR and gas porosimetry on extracted plugs from cores. Note this require that the samples are well-preserved and retain the native irreducible fluids.

Various mathematical symbols used throughout this disclosure are listed with their description in TABLE 1 below.

TABLE 1

Figure 4A:
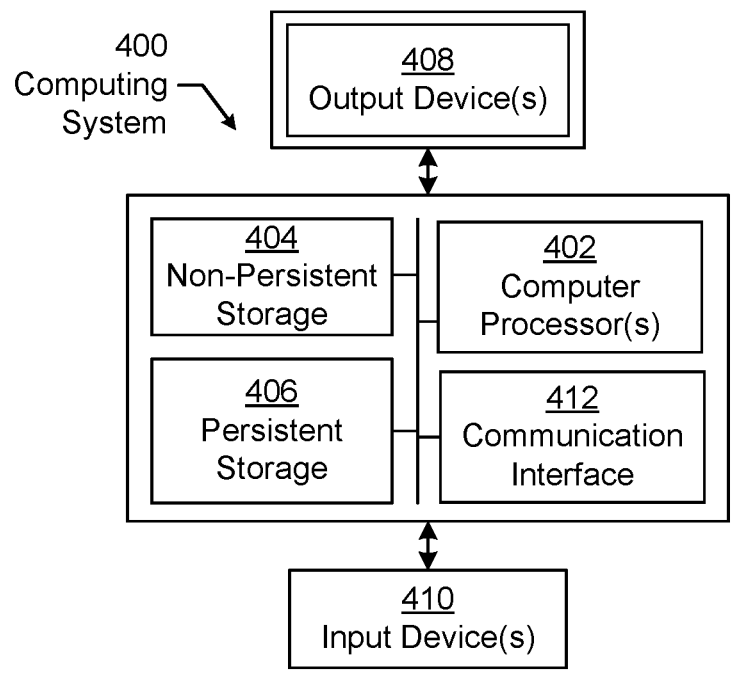
FIGS. 4A and 4B show a computing system in accordance with one or more embodiments.

EMR: estimated maximum recoverable
MRHC: maximum recoverable hydrocarbon
ISHC: in-situ hydrocarbon in the source rocks
$\phi$: total porosity
$\phi_w$: the volume of water in porosity unit
$\phi_{HC}$: the volume of hydrocarbon in porosity unit at reservoir condition
$\phi_{HC}^{rem}$: remaining hydrocarbon in porosity unit at surface condition
$\phi_{HC}^{prod}$: produced hydrocarbon in porosity unit at surface condition
$v_w$: measured NMR water signal in the reservoir calibrated to volume unit
$v_{HC}$: measured NMR hydrocarbon signal calibrated to volume unit
$HI_w^{res}$: hydrogen index of water at reservoir condition
$HI_{HC}^{res}$: hydrogen index of hydrocarbon at reservoir condition
$\phi_{pres.\ core}^{NMR}$: fluid in the preserved cores in porosity unit
$S_w$: water saturation Embodiments disclosed herein may be implemented on a computing system. Any combination of mobile device, desktop, server, router, switch, embedded device, or other types of hardware may be used. For example, the downhole data and core sample analysis engine (307) and EMR analysis engine (308) depicted in FIG. 1B above may be implemented using computer processors and software instructions of such computing system to analyze and generate the aforementioned EMR result. Similarly, various stored data in the buffer (301) depicted in FIG. 1B above may be implemented using persistent and/or non-persistent storages of such computing system. Further, the downhole data and core sample analysis engine (307) and EMR analysis engine (308) may receive inputs from and send control signals/commands to the well control system (126) and/or other part of the well system (106) depicted in FIG. 1A above using the communication interface of such computing system. As shown in FIG. 4A, the computing system (400) may include one or more computer processors (402), non-persistent storage (404) (e.g., volatile memory, such as random access memory (RAM), cache memory), persistent storage (406) (e.g., a hard disk, an optical drive such as a compact disk (CD) drive or digital versatile disk (DVD) drive, a flash memory, etc.), a communication interface (412) (e.g., Bluetooth interface, infrared interface, network interface, optical interface, etc.), and numerous other elements and functionalities.

The computer processor(s) (402) may be an integrated circuit for processing instructions. For example, the computer processor(s) may be one or more cores or micro-cores of a processor. The computing system (400) may also include one or more input devices (410), such as a touchscreen, keyboard, mouse, microphone, touchpad, electronic pen, or any other type of input device.

The communication interface (412) may include an integrated circuit for connecting the computing system (400) to a network (not shown) (e.g., a local area network (LAN), a wide area network (WAN) such as the Internet, mobile network, or any other type of network) and/or to another device, such as another computing device.

Further, the computing system (400) may include one or more output devices (408), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (402), non-persistent storage (404), and persistent storage (406). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

Figure 4B:
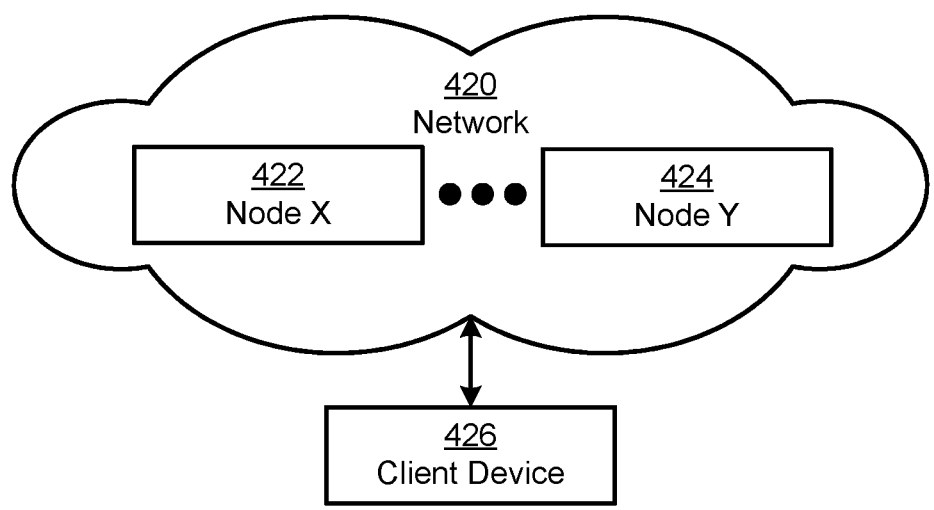

The computing system (400) in FIG. 4A may be connected to or be a part of a network. For example, as shown in FIG. 4B, the network (420) may include multiple nodes (e.g., node X (422), node Y (424)). Each node may correspond to a computing system, such as the computing system shown in FIG. 4A, or a group of nodes combined may correspond to the computing system shown in FIG. 4A. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system (400) may be located at a remote location and connected to the other elements over a network.

Although not shown in FIG. 4B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (for example, node X (422), node Y (424)) in the network (420) may be configured to provide services for a client device (426). For example, the nodes may be part of a cloud computing system. The nodes may include functionality to receive requests from the client device (426) and transmit responses to the client device (426). The client device (426) may be a computing system, such as the computing system shown in FIG. 4A. Further, the client device (426) may include or perform all or a portion of one or more embodiments of the disclosure.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

What is claimed is:

1. A method for determining maximum recoverable hydrocarbon (EMR) in a tight reservoir, the method comprising:
   drilling a formation at a candidate location while measuring formation properties to generate downhole logs;
   determining, based on the downhole logs, a total measure of hydrocarbon amount at the candidate location within the tight reservoir;
   bringing a core sample created by said drilling to the Earth's surface;
   performing, NMR analysis of the core sample to determine, by at least attributing fluid loss during core surfacing of the core sample to hydrocarbons, a non-recoverable measure of hydrocarbon amount within the core sample of the tight reservoir;
   determining an EMR measure based on the total measure of hydrocarbon amount and the non-recoverable measure of hydrocarbon amount; and
   continuing, based on the EMR measure exceeding a pre-determined threshold, said drilling to complete a well at the candidate location of the tight reservoir, wherein during the core surfacing pore pressure reduces from a reservoir condition to a surface condition.

2. The method of claim 1, wherein the total measure of hydrocarbon amount is determined based on $\phi_w = v_w / HI_w^{res}$, $\phi_{HC} = v_{HC} / HI_{HC}^{res}$, where and denote a water volume percentage, a hydrocarbon volume percentage, a hydrogen index of water, and the hydrogen index of the hydrocarbons, respectively, at reservoir condition that are determined based on nuclear magnetic resonance (NMR) logging data of the downhole logs, where $HI_w^{res}$ and $HI_{HC}^{res}$ denote hydrogen indices of water and the hydrocarbons at reservoir condition that are determined based on the NMR logging data, and where $v_w$ and $v_{HC}$ denotes measured NMR signals from water and hydrocarbon, respectively in the NMR logging data.

3. The method of claim 1, wherein the non-recoverable measure of hydrocarbon amount is determined based on $\phi_{pres.core}^{NMR} = \phi_w + \phi_{HC}^{rem}$, where $\phi_{pres.core}^{NMR}$ denotes a fluid volume percentage in the core sample measured at surface condition using an NMR method, and where $\phi_w$ and $\phi_{HC}^{rem}$ denote a water volume percentage and a non-recoverable hydrocarbon volume percentage, respectively, in the core sample measured at surface condition.

4. The method of claim 1, wherein the EMR measure is determined based on $EMR = (\phi_w + \phi_{HC} HI_{HC}^{res} - \phi_{pres.core}^{NMR}) / \phi_{HC} HI_{HC}^{res}$, where $\phi_w$ and $\phi_{HC}$ denote a water volume percentage and a hydrocarbon volume percentage, respectively, at reservoir condition that are determined based on nuclear magnetic resonance (NMR) logging data of the downhole logs, $\phi_{pres.core}^{NMR}$ denotes a fluid volume percentage in the core sample measured at surface condition using an NMR method, and $HI_{HC}^{res}$ denotes a hydrogen index of the hydrocarbons.

5. The method of claim 1, wherein the EMR measure is determined based on $EMR = [S_w + (1-S_w) HI_{HC}^{res} - \phi_{pres.core}^{NMR} / \phi] / (1-S_w) HI_{HC}^{res}$, where $S_w$ denotes a water saturation measured at reservoir condition using the downhole logs, $\phi_{pres.core}^{NMR}$ denotes a fluid volume percentage in the core sample measured at surface condition using an NMR method, and $HI_{HC}^{res}$ denotes a hydrogen index of the hydrocarbons.

6. The method of claim 1, wherein the hydrocarbons and water are in liquid states in the tight reservoir, wherein the EMR measure is determined based on $EMR = (1 - \phi_{pres.core}^{NMR} / \phi) / (1-S_w)$, where $S_w$ denotes a water saturation measured at reservoir condition using the downhole logs, $\phi_{pres.core}^{NMR}$ denotes a fluid volume percentage in the core sample measured at surface condition using an NMR method.

7. The method of claim 1, wherein the EMR measure is one of a plurality of EMRs that are determined based on a plurality of rock samples extracted at a plurality of depths in the tight reservoir, the method further comprising computing an overall EMR by at least averaging the plurality of EMRs.

8. A system comprising:
   a tight reservoir;
   a data repository for storing downhole logs of the tight reservoir; an analysis and modeling engine comprising functionality for:
   determining, based on the downhole logs, a total measure of hydrocarbon amount at a candidate location within the tight reservoir;
   determining, by at least attributing fluid loss during core surfacing of the core sample to hydrocarbons, a non-recoverable measure of hydrocarbon amount within a core sample of the tight reservoir; and
   determining an EMR measure based on the total measure of hydrocarbon amount and the non-recoverable measure of hydrocarbon amount; and
   a well system for drilling a formation at the candidate location while measuring formation properties to generate the downhole logs; bringing a core sample created by said drilling to the Earth's surface;
   performing, NMR analysis of the core sample for said determining the non-recoverable measure of hydrocarbon amount within the core sample; and
   continuing, based on the EMR measure exceeding a pre-determined threshold, said drilling to complete a well at the candidate location of the tight reservoir, wherein during the core surfacing pore pressure reduces from a reservoir condition to a surface condition.

9. The system of claim 8, wherein the total measure of hydrocarbon amount is determined based on $\phi_w = v_w / HI_w^{res}$, $\phi_{HC} = v_{HC} / HI_{HC}^{res}$, where $\phi_w$, $\phi_{HC}$, $HI_w^{res}$, and $HI_{HC}^{res}$ denote a water volume percentage, a hydrocarbon volume percentage, a hydrogen index of water, and the hydrogen index of the hydrocarbons, respectively, at reservoir condition that are determined based on nuclear magnetic resonance (NMR) logging data of the downhole logs, where $HI_w^{res}$ and $HI_{HC}^{res}$ denote hydrogen indices of water and the hydrocarbons at reservoir condition that are determined based on the NMR logging data, and where $v_w$ and $v_{HC}$ denotes measured NMR signals from water and hydrocarbon, respectively in the NMR logging data.

10. The system of claim 8, wherein the non-recoverable measure of hydrocarbon amount is determined based on $\phi_{pres.core}^{NMR} = \phi_w + \phi_{HC}^{rem}$, where $\phi_{pres.core}^{NMR}$ denotes a fluid volume percentage in the core sample measured at surface condition using an NMR method, and where $\phi_w$ and $\phi_{HC}^{rem}$ denote a water volume percentage and a non-recoverable hydrocarbon volume percentage, respectively, in the core sample measured at surface condition.

11. The system of claim 8, wherein the EMR measure is determined based on $EMR = (\phi_w + \phi_{HC} HI_{HC}^{res} - \phi_{pres.core}^{NMR})/\phi_{HC} HI_{HC}^{res}$, where $\phi_w$ and $\phi_{HC}$ denote a water volume percentage and a hydrocarbon volume percentage, respectively, at reservoir condition that are determined based on nuclear magnetic resonance (NMR) logging data of the downhole logs, $\phi_{pres.core}^{NMR}$ denotes a fluid volume percentage in the core sample measured at surface condition using an NMR method, and $HI_{HC}^{res}$ denotes a hydrogen index of the hydrocarbons.

12. The system of claim 8, wherein the EMR measure is determined based on $EMR = [S_w + (1-S_w)HI_{HC}^{res} - \phi_{pres.core}^{NMR}/\phi]/(1-S_w)HI_{HC}^{res}$, where $S_w$ denotes a water saturation measured at reservoir condition using the downhole logs, $\phi_{pres.core}^{NMR}$ denotes a fluid volume percentage in the core sample measured at surface condition using an NMR method, and $HI_{HC}^{res}$ denotes a hydrogen index of the hydrocarbons.

13. The system of claim 8, wherein the hydrocarbons and water are in liquid states in the tight reservoir, wherein the EMR measure is determined based on $EMR = (1-\phi_{pres.core}^{NMR}/\phi)/(1-S_w)$, where $S_w$ denotes a water saturation measured at reservoir condition using the downhole logs, $\phi_{pres.core}^{NMR}$ denotes a fluid volume percentage in the core sample measured at surface condition using an NMR method.

14. The system of claim 8, wherein the EMR measure is one of a plurality of EMRs that are determined based on a plurality of rock samples extracted at a plurality of depths in the tight reservoir, the method further comprising computing an overall EMR by at least averaging the plurality of EMRs.

15. A non-transitory computer readable medium (CRM) storing computer readable program code for determining maximum recoverable hydrocarbon (EMR) in a tight reservoir, wherein the computer readable program code, when executed by a computer, comprises functionality for:

drilling a formation at a candidate location while measuring formation properties to generate downhole logs;

determining, based on the downhole logs, a total measure of hydrocarbon amount at the candidate location within the tight reservoir;

bringing a core sample created by said drilling to the Earth's surface;

performing, NMR analysis to determine, by at least attributing fluid loss during core surfacing of the core sample to hydrocarbons, a non-recoverable measure of hydrocarbon amount within the core sample of the tight reservoir;

determining an EMR measure based on the total measure of hydrocarbon amount and the non-recoverable measure of hydrocarbon amount; and continuing, based on the EMR measure exceeding a pre-determined threshold, said drilling to complete a well at the candidate location of the tight reservoir, wherein during the core surfacing pore pressure reduces from a reservoir condition to a surface condition.

16. The non-transitory CRM of claim 15, wherein the total measure of hydrocarbon amount is determined based on $\phi_w = v_w/HI_w^{res}$, $\phi_{HC} = v_{HC}/HI_{HC}^{res}$, where $\phi_w$, $\phi_{HC}$, $HI_w^{res}$, and $HI_{HC}^{res}$ denote a water volume percentage, a hydrocarbon volume percentage, a hydrogen index of water, and the hydrogen index of the hydrocarbons, respectively, at reservoir condition that are determined based on nuclear magnetic resonance (NMR) logging data of the downhole logs, where $HI_w^{res}$ and $HI_{HC}^{res}$ denote hydrogen indices of water and the hydrocarbons at reservoir condition that are determined based on the NMR logging data, and where $v_w$ and $v_{HC}$ denotes measured NMR signals from water and hydrocarbon, respectively in the NMR logging data.

17. The non-transitory CRM of claim 15, wherein the non-recoverable measure of hydrocarbon amount is determined based on $\phi_{pres.core}^{NMR} = \phi_w + \phi_{HC}^{rem}$, where $\phi_{pres.core}^{NMR}$ denotes a fluid volume percentage in the core sample measured at surface condition using an NMR method, and where $\phi^w$ and $\phi_{HC}^{rem}$ denote a water volume percentage and a non-recoverable hydrocarbon volume percentage, respectively, in the core sample measured at surface condition.

18. The non-transitory CRM of claim 15, wherein the EMR measure is determined based on $EMR = (\phi_w + \phi_{HC} HI_{HC}^{res} - \phi_{pres.core}^{NMR})/\phi_{HC} HI_{HC}^{res}$, where $\phi_w$ and $\phi_{HC}$ denote a water volume percentage and a hydrocarbon volume percentage, respectively, at reservoir condition that are determined based on nuclear magnetic resonance (NMR) logging data of the downhole logs, $\phi_{pres.core}^{NMR}$ denotes a fluid volume percentage in the core sample measured at surface condition using an NMR method, and $HI_{HC}^{res}$ denotes a hydrogen index of the hydrocarbons.

19. The non-transitory CRM of claim 15, wherein the EMR measure is determined based on $EMR = [S_w + (1-S_w)HI_{HC}^{res}\phi_{pres.core}^{NMR}/\phi]/(1-S_w)HI_{HC}^{res}$, where $S_w$ denotes a water saturation measured at reservoir condition using the downhole logs, $\phi_{pres.core}^{NMR}$ denotes a fluid volume percentage in the core sample measured at surface condition using an NMR method, and $HI_{HC}^{res}$ denotes a hydrogen index of the hydrocarbons.

20. The non-transitory CRM of claim 15, wherein the hydrocarbons and water are in liquid states in the tight reservoir, wherein the EMR measure is determined based on $EMR = (1-\phi_{pres.core}^{NMR}/\phi)/(1-S_w)$, where $S_w$ denotes a water saturation measured at reservoir condition using the downhole logs, $\phi_{pres.core}^{NMR}$ denotes a fluid volume percentage in the core sample measured at surface condition using an NMR method.

* * * * *